US012048295B2

United States Patent
Halachmi et al.

(10) Patent No.: US 12,048,295 B2
(45) Date of Patent: Jul. 30, 2024

(54) METHOD AND APPARATUS FOR MONITORING FOOD INTAKE OF LIVESTOCK ANIMALS

(71) Applicant: The State of Israel, Ministry of Agriculture & Rural Development, Agricultural Research Organization (ARO) (Volcani Center), Rishon-LeZion (IL)

(72) Inventors: Ilan Halachmi, Kfar-Yehoshua (IL); Victor Bloch, Jerusalem (IL); Harel Levit, Nahalal (IL); Ehud Ram, Kfar-Saba (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 296 days.

(21) Appl. No.: 16/765,903

(22) PCT Filed: Nov. 22, 2018

(86) PCT No.: PCT/IL2018/051272
§ 371 (c)(1),
(2) Date: May 21, 2020

(87) PCT Pub. No.: WO2019/102471
PCT Pub. Date: May 31, 2019

(65) Prior Publication Data
US 2020/0305388 A1 Oct. 1, 2020

Related U.S. Application Data

(60) Provisional application No. 62/589,605, filed on Nov. 22, 2017.

(51) Int. Cl.
*A01K 5/02* (2006.01)
*A01K 29/00* (2006.01)
(Continued)

(52) U.S. Cl.
CPC .......... *A01K 5/0283* (2013.01); *A01K 5/0275* (2013.01); *A01K 29/005* (2013.01);
(Continued)

(58) Field of Classification Search
CPC ...... A01K 5/02; A01K 5/0275; A01K 5/0283; A01K 11/006; A01K 29/005
(Continued)

(56) References Cited

U.S. PATENT DOCUMENTS

| 5,309,864 A | 5/1994 | Harmsen et al. |
| 5,711,246 A | 1/1998 | Yano et al. |

(Continued)

FOREIGN PATENT DOCUMENTS

| CN | 1233148 | 10/1999 |
| CN | 202565957 | 12/2012 |

(Continued)

OTHER PUBLICATIONS

Communication Pursuant to Article 94(3) EPC Dated Jan. 3, 2019 From the European Patent Office Re. Application No. 14867339.5. (9 Pages).
(Continued)

*Primary Examiner* — David J Parsley

(57) ABSTRACT

A system for monitoring individual food intake of a livestock animal includes a calibration system configured to measure weight or volume of food intake of an animal over a pre-defined period of time and to calibrate a mathematical model for the animal based on the measure, a tracking system configured track animal eating behavior at times other than the pre-defined period of time and a computing
(Continued)

system. The pre-defined period of time is less than three weeks. The mathematical model relates eating behavior of the animal and defined physiological parameters of the animal with food intake. The computing system determines food intake of the animal over a lactation period based on the mathematical model for the animal as calibrated and the eating behavior at the times other than the pre-defined period of time.

22 Claims, 11 Drawing Sheets

(51) Int. Cl.
  *G06N 7/00*   (2023.01)
  *G06Q 10/063*  (2023.01)
  *G06Q 50/02*  (2012.01)
  *G06T 7/50*   (2017.01)
(52) U.S. Cl.
  CPC .............. *G06N 7/00* (2013.01); *G06Q 10/063* (2013.01); *G06Q 50/02* (2013.01); *G06T 7/50* (2017.01)
(58) Field of Classification Search
  USPC ...................................... 119/51.02, 719–721
  See application file for complete search history.

(56) References Cited

U.S. PATENT DOCUMENTS

| | | | |
|---|---|---|---|
| 6,427,627 | B1 | 8/2002 | Huisma |
| 6,651,585 | B2 | 11/2003 | van den Berg |
| 6,868,804 | B1 | 3/2005 | Huisma et al. |
| 6,997,140 | B2 | 2/2006 | Finlayson |
| 7,296,536 | B2 | 11/2007 | Umeg?rd |
| 7,350,481 | B2 * | 4/2008 | Bar-Shalom ......... A01K 29/005 119/859 |
| 7,370,606 | B2 | 5/2008 | van der Lely et al. |
| 8,019,633 | B2 | 9/2011 | Stroman et al. |
| 8,037,846 | B2 | 10/2011 | Pratt |
| 8,282,557 | B2 | 10/2012 | Haynes et al. |
| 9,167,800 | B2 | 10/2015 | Spicola et al. |
| 10,085,419 | B2 | 10/2018 | Zimmerman et al. |
| 10,127,747 | B2 | 11/2018 | Spittle et al. |
| 2007/0137584 | A1 * | 6/2007 | Travis ...................... A01K 5/02 119/51.02 |
| 2008/0252464 | A1 | 10/2008 | Panasevich |
| 2012/0221250 | A1 * | 8/2012 | Cottle .................. A01K 29/005 702/19 |
| 2017/0013802 | A1 | 1/2017 | Zimmerman et al. |
| 2017/0118961 | A1 | 5/2017 | Halachmi et al. |

FOREIGN PATENT DOCUMENTS

| | | |
|---|---|---|
| CN | 202773709 | 3/2013 |
| CN | 103053437 | 4/2013 |
| CN | 103065222 | 4/2013 |
| CN | 105594611 | 5/2016 |
| CN | 105960164 | 9/2016 |
| EP | 0657098 | 6/1995 |
| EP | 0673600 | 9/1995 |
| IL | 110109 | 10/1994 |
| IL | 119109 | 11/1996 |
| NZ | 581453 | 10/2011 |
| WO | WO 01/67853 | 9/2001 |
| WO | WO 2008/135546 | 11/2008 |
| WO | WO 2010/059161 | 5/2010 |
| WO | WO 2011/020145 | 2/2011 |
| WO | WO 2013/005038 | 1/2013 |
| WO | WO 2015/083176 | 6/2015 |
| WO | WO 2019/102471 | 5/2019 |

OTHER PUBLICATIONS

Communication Pursuant to Article 94(3) EPC Dated Oct. 9, 2019 From the European Patent Office Re. Application No. 14867339.5. (9 Pages).
Communication Pursuant to Article 94(3) EPC Dated Jun. 18, 2020 From the European Patent Office Re. Application No. 14867339.5. (9 Pages).
Communication Pursuant to Article 94(3) EPC Dated Apr. 19, 2018 From the European Patent Office Re. Application No. 14867339.5. (7 Pages).
Decision on Rejection Dated Nov. 12, 2019 From the National Intellectual Property Administration of the People's Republic of China Re. Application No. 201480075095.1 and Its Translation Into English. (13 Pages).
International Preliminary Report on Patentability Dated Jun. 4, 2020 From the International Bureau of WIPO Re. Application No. PCT/IL2018/051272. (10 Pages).
International Preliminary Report on Patentability Dated Jun. 23, 2016 From the International Bureau of WIPO Re. Application No. PCT/IL2014/051071.
International Search Report and the Written Opinion Dated Feb. 25, 2019 From the International Searching Authority Re. Application No. PCT/IL2018/051272. (14 Pages).
International Search Report and the Written Opinion Dated Mar. 31, 2015 From the International Searching Authority Re. Application No. PCT/IL2014/051071.
Notification of Office Action and Search Report Dated Jun. 19, 2018 From the State Intellectual Property Office of the People's Republic of China Re. Application No. 201480075095.1 and Its Translation Into English. (24 Pages).
Notification of Office Action Dated Mar. 4, 2019 From the National Intellectual Property Administration of the People's Republic of China Re. Application No. 201480075095.1 and Its Translation Into English. (13 Pages).
Office Action Dated Jan. 22, 2020 From the Israel Patent Office Re. Application No. 246138 and Its Translation Into English. (5 Pages).
Office Action Dated Jan. 31, 2019 From the Israel Patent Office Re. Application No. 246138 and Its Translation Into English. (5 Pages).
Official Action Dated Jun. 3, 2019 From the US Patent and Trademark Office Re. U.S. Appl. No. 15/102,293. (23 Pages).
Supplementary European Search Report and the European Search Opinion Dated Jun. 13, 2017 From the European Patent Office Re. Application No. 14867339.5. (9 Pages).
Ben Meir et al. "Eating Behavior, Milk Production, Rumination, and Digestibility Characteristics of High- and Low-Efficiency Lactating Cows Fed A Low-Roughage Diet", Journal of Daiy Science, 101: 10973-10984, Published Online Sep. 27, 2018.
Halachmi et al. "A Real-Time Control System for Individual Dairy Cow Food Intake", Computers and Electronics in Agriculture, 20(2): 131-144, Jul. 1998.
Halachmi et al. "Feed Intake of Holstein, Danish Red, and Jersey Cows in Automatic Milk Systems", Livestock Science, 138(1-3): 56-61, Jun. 2011.
Halachmi et al. "Predicting Feed Intake of the Individual Dairy Cow", Journal of Dairy Science, 87(7): 2254-2267, 2004.
Herd et al. "Reducing the Cost of Beef Production Through Genetic Improvement in Residual Feed Intake: Opportunity and Challenges to Application", Journal of Animal Science, 81(E Suppl.1): E9-E17, Jan. 2003.
Maltz et al. "Effect of Feeding According to Energy Balance on Performance, Nutrient Excretion, and Feeding Behavior of Early Lactation Dairy Cows", Journal of Dairy Science, 96: 5249-5266, 2013.
English Summary Dated Aug. 10, 2021 of Notification of Office Action Dated Jul. 19, 2021 From the State Intellectual Property Office of the People's Republic of China Re. Application No. 201880086108.3. (5 Pages).
Notification of Office Action and Search Report Dated Jul. 19, 2021 From the State Intellectual Property Office of the People's Republic of China Re. Application No. 201880086108.3. (16 Pages).

(56) References Cited

OTHER PUBLICATIONS

Notification of Office Action Dated Aug. 23, 2021 From the State Intellectual Property Office of the People's Republic of China Re. Application No. 201480075095.1 and Its Translation into English. (24 Pages).
Supplementary European Search Report and the European Search Opinion Dated Jun. 25, 2021 From the European Patent Office Re. Application No. 18881447.9. (7 Pages).
Decision of Reexamination Dated Dec. 29, 2021 From the National Intellectual Property Administration of the People's Republic of China Re. Application No. 201480075095.1 and Its Translation Into English. (23 Pages).
Notification of Office Action Dated Apr. 2, 2022 From the State Intellectual Property Office of the People's Republic of China Re. Application No. 201880086108.3 and Its Translation Into English. (6 Pages).
Communication Pursuant to Article 94(3) EPC Dated Dec. 9, 2022 From the European Patent Office Re. Application No. 18881447.9. (9 Pages).
Office Action Dated Feb. 9, 2023 From the Israel Patent Office Re. Application No. 274850. (5 Pages).
Notification of Office Action and Search Report Dated Mar. 30, 2023 From the State Intellectual Property Office of the People's Republic of China Re. Application No. 202210299694.8 and Its Translation Into English. (26 Pages).
Communication Pursuant to Article 94(3) EPC Dated Aug. 29, 2023 From the European Patent Office Re. Application No. 14867339.5. (5 Pages).
Office Action Dated Nov. 15, 2023 From the Israel Patent Office Re. Application No. 274850. (4 Pages).
Notification of Office Action Dated Jan. 30, 2024 From the National Intellectual Property Administration of the People's Republic of China Re. Application No. 202210299694.8 and Its Translation Into English. (32 Pages).

\* cited by examiner

METHOD AND APPARATUS FOR MONITORING FOOD INTAKE OF LIVESTOCK ANIMALS

RELATED APPLICATIONS

This application is a National Phase of PCT Patent Application No. PCT/IL2018/051272 having International filing date of Nov. 22, 2018, which claims the benefit of priority under 35 USC § 119(e) of U.S. Provisional Patent Application No. 62/589,605 filed on Nov. 22, 2017. The contents of the above applications are all incorporated by reference as if fully set forth herein in their entirety.

FIELD AND BACKGROUND OF THE INVENTION

The present invention, in some embodiments thereof, relates to livestock management and, more particularly, but not exclusively, to monitoring food intake of cattle on an individual animal basis.

Measurement of the individual livestock food intake is important for improving the efficiency of livestock farms such as for example dairy farms. The information about the food intake of a specific animal in a farm reflects the health condition of the animal and defines its effectiveness.

A known method for the food intake measure uses an individual measuring station including two main systems: Feed measuring, usually scales or volume measuring devices and individual animal identifying system, usually RFID. Effective measurement based on this method without intervention into the animal feeding behavior may be achieved when the number of the measuring stations in a farm corresponds to the number of the animals. Since even small farms typically include one hundred or more animals, the cost associated with measuring food intake may render such a method infeasible on a commercial scale. Furthermore, the bins containing the weighed feed change the infrastructure of the farms and require additional time consuming operations, such as cleaning of the bins, cleaning the feed remnants around the bins, and adopting the feed distribution system. This may add further costs.

Some alternative methods have been suggested in an attempt to reduce the total price of food intake measuring systems. In one example, it has been suggested to use volume feed measuring based on captured images of the fodder as an alternative to mass feed measuring. In another example, it has been suggested to use biometric identification as an alternative to RFID identification to identify a cow at a feeding station. However, a reliable and cost effective measuring system that may be used in a commercial scale based on such methods has not been established.

SUMMARY OF THE INVENTION

According to an aspect of some embodiments of the present invention there is provided a method and system to determine individual food (dry matter food) intake of animals in an entire herd while only monitoring fodder weight or volume in only small part of a feed lane from which the herd feeds. Optionally, fodder weight or volume is monitored in less than 20% or less than 10% of the feeding stations. Animals may be monitored on a rotation basis by selectively placing animals in the calibrating area for a pre-defined time period. In some example embodiments, a mathematical model relating food intake to physiological parameters of an individual animal is applied to determine efficiency of the animal over an entire lactation period based on measuring food intake of an individual animal for only a short period in the lactation period of the animal. According to some example embodiments, efficiency data may be used to select animals for breeding, select animals to be removed from the herd, select fodder quality for individual animals or groups and may also be applied to generally evaluate the individual animal and the herd.

According to an aspect of some embodiments of the present invention there is provided a weighing system for an individual feeding station in a livestock farm. According to some example the weighing system is configured for low cost and convenience.

According to some aspects of the present disclosure, there is provided a system for monitoring individual food intake of a livestock animal comprising: a calibration system configured to measure weight or volume of food intake of an animal over a pre-defined period of time and to calibrate a mathematical model for the animal based on the measure, wherein the mathematical model relates eating behavior of the animal and defined physiological parameters of the animal with food intake, wherein the pre-defined period of time is less than three weeks; a tracking system configured track animal eating behavior at times other than the pre-defined period of time; and a computing system configured to determine food intake of the animal over a lactation period based on the mathematical model for the animal as calibrated and the eating behavior at the times other than the pre-defined period of time.

Optionally, the calibration system is configured to service less than 20% of the livestock animals at a time.

Optionally, the calibration system is configured to be stationed in an isolated portion of an animal shed.

Optionally, tracking system is installed in a common feeding lane in a portion of the animal shed that is not isolated.

Optionally, the calibration system includes a plurality of individual feeding stations, each integrated with a scale.

Optionally, at least one of the plurality of individual feeding stations includes a feeding bin suspended from a frame with a first cable, and wherein the feeding station includes a load cell connected to the first cable.

Optionally, a second cable is connected at one end to the feeding bin and at another end to a lifting mechanism, wherein the lifting mechanism is configured to tilt the feeding bin and expel the food in the feeding bin based on pulling the second cable.

Optionally, the feeding bin includes clearing plate that rotatable connected to the feeding bin, wherein the clearing plate is configured to rotate during tilting of the feeding bin.

Optionally, the calibration system comprises an imaging system configured to detect volume of fodder.

Optionally, the imaging system includes at least one depth camera.

Optionally, the imaging system includes a plurality of cameras.

Optionally, the imaging system is configured to apply a photogrammetric method to detect the volume.

Optionally, the calibration system comprises a scale configured to monitor weight of a sample volume of fodder.

Optionally, the calibration system comprises an identification system configured to identify an animal eating and to monitor eating behavior of the animal.

Optionally, the identification system is configured to identify the animal based on imaging a dedicated symbol on a collar of the animal, biometric verification or RFID.

Optionally, the calibration system comprises a computing system configured to calibrate the mathematical model.

Optionally, the computing system is configured to access physiological data related to the animal.

Optionally, the mathematical model is animal specific.

According to some aspects of the present disclosure, there is provided a method for monitoring individual food intake of a livestock animal comprising: measuring food intake of individual animals in a herd for a pre-defined period of time, wherein the pre-defined period of time is less than three weeks; tracking eating behavior of the individual animals during the a pre-defined period of time; calibrating a mathematical model for the animal based on the measure, wherein the mathematical model relates eating behavior of the animal and defined physiological parameters of the animal with food intake; continue tracking animal eating behavior at times other than the pre-defined period of time; and determine food intake of the animal at times other than the pre-defined period of time based on the mathematical model for the animal as calibrated and the eating behavior at the times other than the pre-defined period of time.

Optionally, the method further comprises measuring the food intake of less than 20% of the livestock animals at a time.

Optionally, the method further comprises measuring food intake of other individual animals in the herd at the end of the pre-defined period of time and calibrating the mathematical model for each of the other individual animals over a subsequent pre-defined period.

Optionally, the measuring performed in an isolated portion of an animal shed.

Optionally, the method further comprises calibrating the mathematical model for each animal in the herd over an entire lactation period, wherein the calibrating is performed consecutively on portions of the herd; determining efficiency of each animal in the herd based on its food intake; and reporting the efficiency.

Optionally, the tracking animal eating behavior at times other than the pre-defined period of time is performed in a common feeding lane in a portion of the animal shed that is not isolated.

Optionally, the measuring food intake of individual animals is based on measuring weight of fodder in individual feeding stations.

Optionally, the feeding station is integrated with an identification system configured to identify the animal eating at the feeding station.

Optionally, measuring food intake of individual animals is based on detecting volume of fodder in a feeding lane.

Optionally, the volume is detected based on a photogrammetric method.

Optionally, the feeding lane is integrated with an identification system configured to identify animals eating at the feeding lane.

Optionally, the method further comprises monitoring specific weight of fodder in the feeding lane and determining food intake based on the volume and the specific weight.

Optionally, the mathematical model is animal specific.

Optionally, the defined physiological parameters of the animal includes days in milking, parameters defining milk quality of milk provided by the animal, and weight of the animal.

Optionally, the mathematical model relates amount of time the animal spends active with food intake and wherein the time the animal spends active is tracked.

Optionally, the eating behavior is tracked based on time spent eating and number of meals.

Optionally, the animals are cows.

According to some aspects of the present disclosure, there is provided a method for managing a herd of dairy animals, the method comprising: monitoring food intake of individual animals in the herd over a lactation cycle; monitoring milk yield of the individual animals over the lactation cycle; determining a feed efficiency score of the individual animals based on the food intake and the milk yield; and reporting animals from the herd that score below a pre-defined feed efficiency score.

Optionally, the method further comprises at least one of removing animals from the herd that score below a pre-defined efficiency score and adjusting quality of fodder based on the efficiency score.

Optionally, the method further comprises selecting a bull for artificial inseminating based on the feed efficiency score.

Optionally, monitoring food intake of individual animals in the herd is based on the method described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
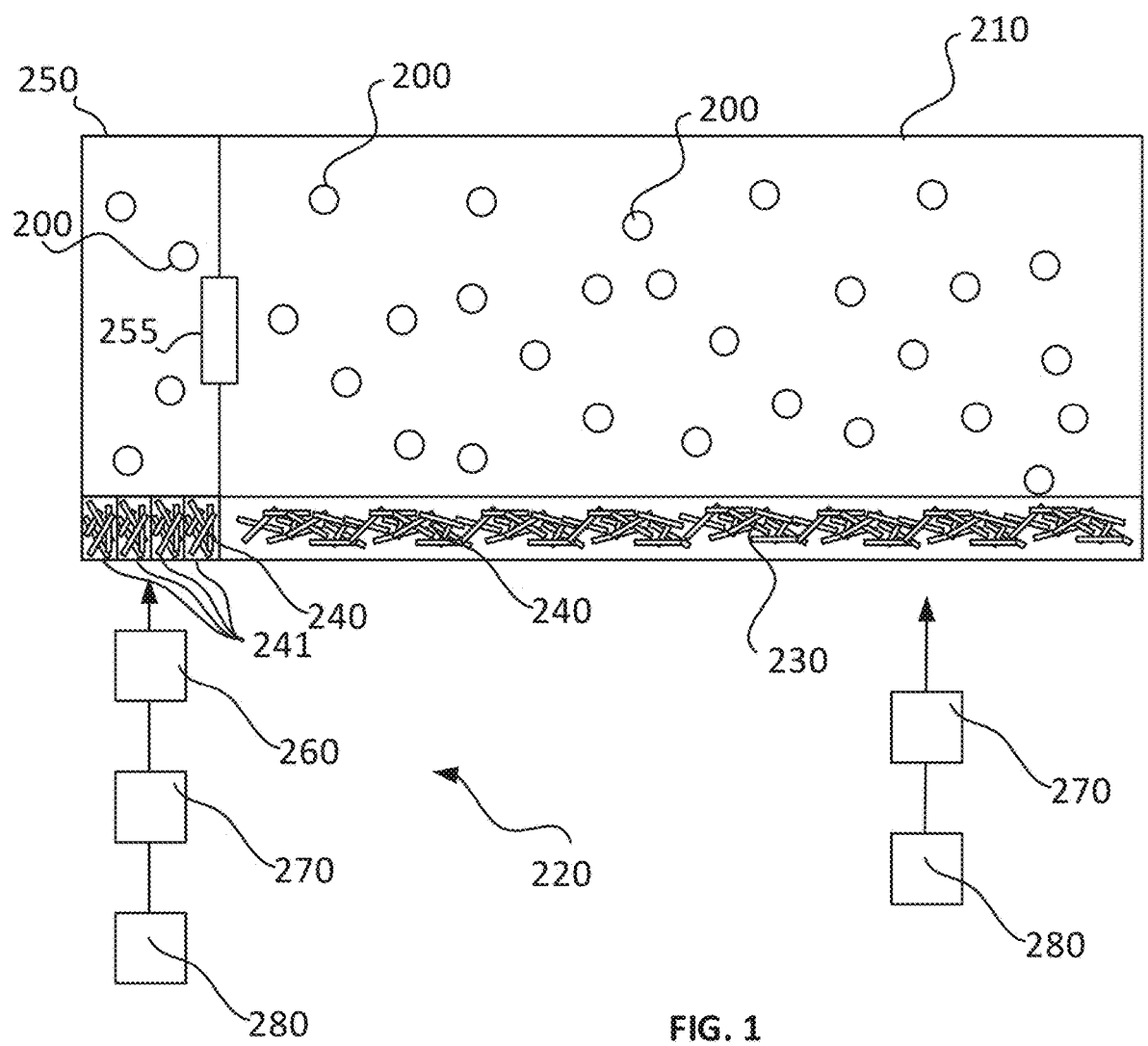
FIG. 1 is a simplified block diagram of an example livestock shelter including a designated food intake calibrating area in accordance with some example embodiments.

The present invention, in some embodiments thereof, relates to livestock management and, more particularly, but not exclusively, to monitoring food intake of cattle on an individual animal basis.

To achieve a precise evaluation of the consumed feed, e.g. dry matter (DM) by a system with lower cost and lower intervention into the farm infrastructure, the exact mass measure by scales with the bins for all animals at all times can be replaced by other methods. According to some example embodiments, there is provided a system for monitoring individual fodder intake and/or efficiency of a dairy animal. According to some example embodiments, part of the evaluation is performed in a designated area in the animal shed or shelter and the animals are placed in turned in the designated area for a pre-defined period of time. The designated area may occupy for example 5%-30% of the shed, e.g. 20%. Optionally, in the general shed area (the non-designated area), eating behavior of individual animals, e.g. eating durations and times may be monitored without measuring weight or volume of food intake so that the animals may freely eat in a more natural environment. Measuring weight or volume only in a designated area may also be more cost efficient as less equipment and processing is required to take measurements on only a portion of the animals at a time as opposed to all the animals all the time. Tracking eating behavior of individual animals, e.g. eating durations and times is less costly and easier than measuring mass of food intake. Optionally, each group of animals is maintained in the designated area for 1-3 weeks, e.g. 2 weeks. Measurements taken while the animal is in the designated area may be used to calibrate a mathematical model that relates food intake of the animal with animal eating behavior and physiological parameters of the animal. Animal eating behavior, e.g. duration and eating times may be monitored throughout the lactation period. Physiological parameters such as weight, milk yield and milk quantity for individual animals are generally tracked in a dairy farm and may be used. Based on the calibrated model, tracked eating behavior and known physiological parameters, food intake of the animal may be monitored over the entire lactation period. In some example embodiments, feed efficiency of the animal is determined based on food intake and milk yield.

Feed efficiency (also referred to as dairy efficiency) may be defined herein as amount of milk produced per amount of dry matter (DM) feed consumed. Feed efficiency (feed to gain or gain to feed ratio) can be a benchmark for profitability. Feed may be measured in varied dimensional units, such as feed energy, kg wet, kg dry matter and more. Milk ("gain") may also be measured in varied dimensional units taking into account milk content such as milk fat, milk protein, milk energy or milk price. It is common that the feed efficiency itself is often dimensionless According to some example embodiments, the designated area includes an identification system configured to identify each animal approaching a feeding station or the feeding lane in the designated area. Identification may be image based or based on RFID. The identification system may also be applied to track eating behavior, e.g. times and duration of eating. In some example embodiments, the designated area includes feeding stations for individual cows that are integrated with scales for measuring weight of the fodder. In some alternate example embodiments, the designated area includes an imaging system configured to monitor volume of fodder in the designated area as well as weighing station to monitor density of the fodder. Individual feeding stations may not be needed when measuring food intake based on volume. Information related to volume and density may be combined to determine the food intake.

In some example embodiments, the designated area may be eliminated and all the animals may be monitored based on monitoring volume of fodder in the entire shed.

According to some example embodiments, there is provided a feeding station including an individual feeding bin that is suspended over the ground. In some example embodiments, a single load cell via which the feeding bin is suspended provides for monitoring weight of fodder in the feeding station. In some example embodiments, the feeding station additionally includes a mechanical system configured to controllably tilt the feeding bin for convenient emptying and cleaning of the feeding bin.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1 is a simplified block diagram of an example livestock shelter including a designated food intake calibrating area in accordance with some example embodiments. A livestock shed 210 or shelter houses a plurality of animals 200, e.g. cows, e.g. 50 to a few hundred animals. Shed 210 typically includes one or more feeding lanes 230 in which fodder 240 is provided. Animals may approach feeding lane 230 to eat. Water stations are also typically provided in shed 210 although not shown here for simplicity. According to some example embodiments, a section 250 of shed 210 is fenced off or isolated and animals 200 may be selectively placed in section 250 for example through a gate 255. In section 250 animals 200 are monitored to detect food intake and parameters related to eating behaviors. All the animals 200 may be placed in section 250 in turn for a pre-defined calibrating period. Monitoring of all the animals 200 may be performed over a full lactation period, e.g. 10-13 months or 11 months. Optionally and depending on the size of the shed, more than one section 250 may be included to accommodate large herds.

According to some example embodiments, section 250 may include individual feeding stations 241, e.g. 2-10 feeding stations 241. Optionally, section 250 is configured with one feeding station 241 for each animal 200 stationed in section 250 at any one time. According to some example embodiments, the food intake calibration system 220 includes a weighing system 260 per feeding station, an identification system 270 configured to identify each cow approaching feeding station 241 and a computing system 280 configured to control the system operation, process data sampled and calibrate a mathematical model relating animal physiological parameters and eating behavior to food intake based on data sampled, e.g. the model defined in Equation 1 herein below. Computing system 280 may include memory capability and may be configured to receive data from other computing systems by wireless or wired connection.

Weight of fodder in feeding stations 241 may be monitored over time. Perturbation in recorded weight may indicate that animal 200 is eating. Eating times, eating duration and quantity consumed may be monitored. Identification device 270 may be based on RFID, may be based on biometric detection or may be based on identifying a visual tag on animal 200. In some example embodiments computing system 280 is configured to store or access physiological data related to each animal 200 in section 250 and may use this information to evaluate animal 200 based on the monitoring. Identification system 270 may also track animal eating behavior, e.g. duration and eating times. Data obtained while the animal is in area 250 may be used to calibrate a model for determining food intake of the animal while the animal is also in area of shed 210, e.g. outside section 250.

According to some example embodiments, eating behavior of animals 200 are tracked in main area of shed 210 to determine some of the parameters of the mathematical model, e.g. number of meals and time spent eating. Optionally, monitoring in main section is with an identification system similar to identification system 270.

Figure 2:
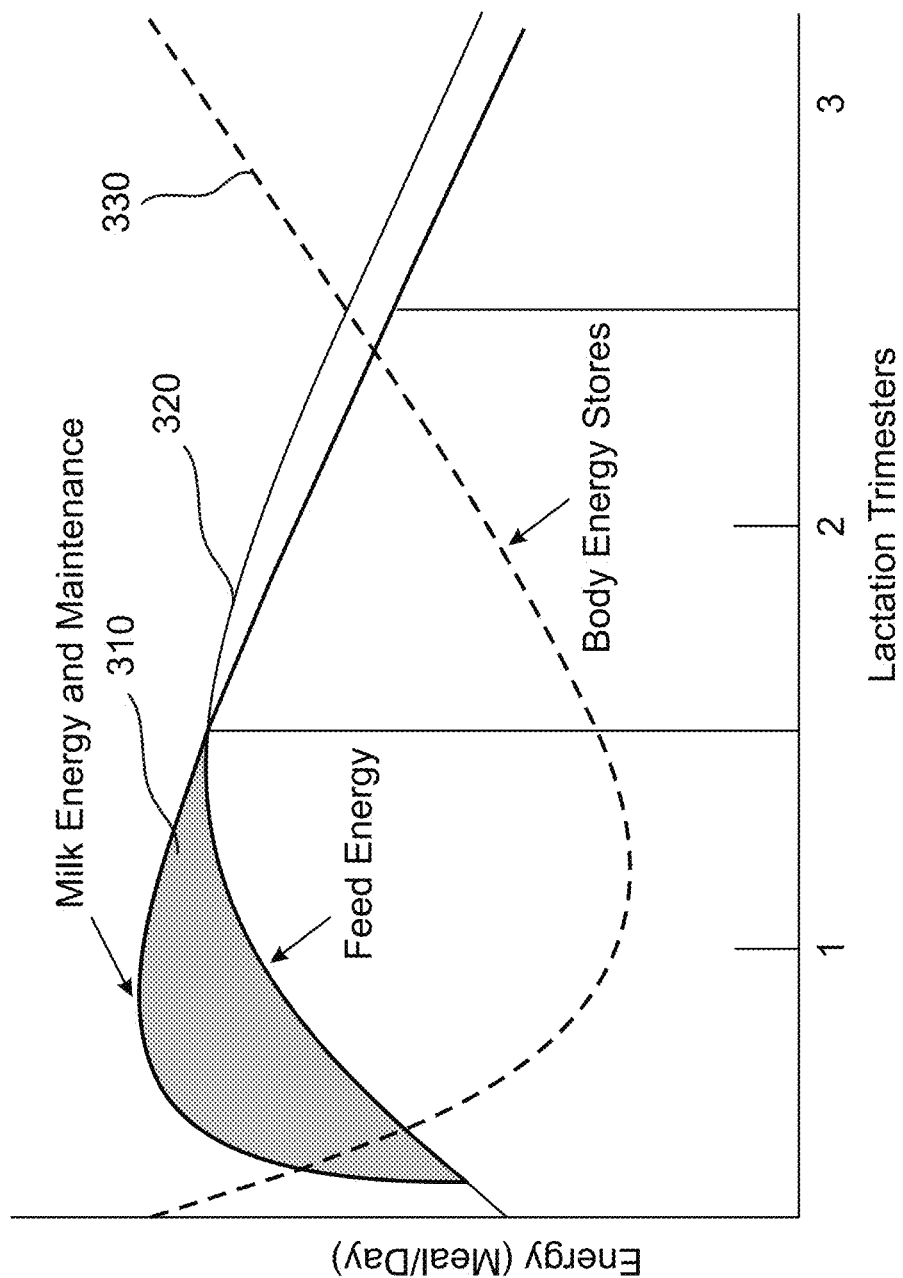
FIG. 2 is an example graph showing change in feed energy over a lactation period of a cow in accordance with some example embodiments.

FIG. 2 is an example graph showing change in feed energy over a lactation period of a cow in accordance with some example embodiments. A cow's food intake, weight and milk production is variable over a lactation period of the cow. Curve 330 represents change in weight of the cow over three lactation trimesters. At the start of a lactation period, weight decreases due to energy spent to support milk production after which there is typically a steady increase in weight. Curve 320 represents food intake which typically increases over the first trimester and then steadily decreases. Curve 310 represents milk production. The difference between milk production energy and food energy may provide insight on animal efficiency. Typically it is desired that a cow provide high milk energy with low food intake.

According to some example embodiments, food intake for each animal is measured for a relatively short part of the lactation cycle. Optionally, the measuring occurs over a 2 week period or a period between 1-3 weeks. In some example embodiments, food intake representative of the entire lactation period may be determined based on output over the calibrating period together with a mathematical model that takes into consideration physiological parameters of the cow and on going eating behavior that is also tracked in the main area of the shed. In some example embodiments, the mathematical model may be defined by the following equation:

$$Y=(\beta_0+\gamma_{0,k}+\delta_{0,j})+(\beta_1+\delta_{1,j})\text{mealTime}_{i,j,k}+ \beta_2\text{numOfMeals}_{i,j,k}+(\beta_3+\delta_{3,j})\text{daysInMilking}_{i,j,k}+ \beta_4\text{fatPercent}_{i,j,k}+\beta_5\text{proteinPercent}_{i,j,k}+ \beta_6\text{lactation}_{i,j,k}+\beta_7\text{MY}_{i,j,k}+\beta_8\text{BW}_{i,j,k}+ \beta_9\text{ratioBWMY}_{i,j,k}+\beta_{10}\text{NRC}_{i,j,k}+\beta_{11}\text{activity}_{i,j,k}+ \varepsilon_{i,j,k} \quad \text{Equation (1)}$$

Where:
  Y Food intake [Kg]
  MY Milk yield [liter or Kg]
  fatPercent Fat percentage in milk [%]
  daysInMilking Days in milking after calving
  proteinPercent Protein percentage in milk [%]
  lactation Number of lactations
  BW (body weight) Automatic weighing of dairy cow [kg]
  MealTime Time spent eating [min]
  numOfMeals Number of meals
  NRC Value of Nutrient Requirements of Dairy Cattle
  ratioBWMY Ratio between body weight and milk yield
  Activity The amount of time the cow spends active [min]

According to some example embodiments, coefficients $\beta$, $\gamma$, $\delta$ and $\varepsilon$ are coefficients of a linear mixed model that may be determined for an individual animal over the calibration period based on repeated measurements of food intake for the animal. The mathematical model may then be applied for that animal to determine ongoing food intake based on eating behavior and known physiological parameters. In this manner animals that are monitored over different stages in the lactation cycle may still be compared (at the end of the lactation cycle) to determine differences in efficiency between the animals. Mathematical model defined in Equation 1 may be calibrated per animal 200 and applied to determined food intake in the main shed area.

Figure 3:
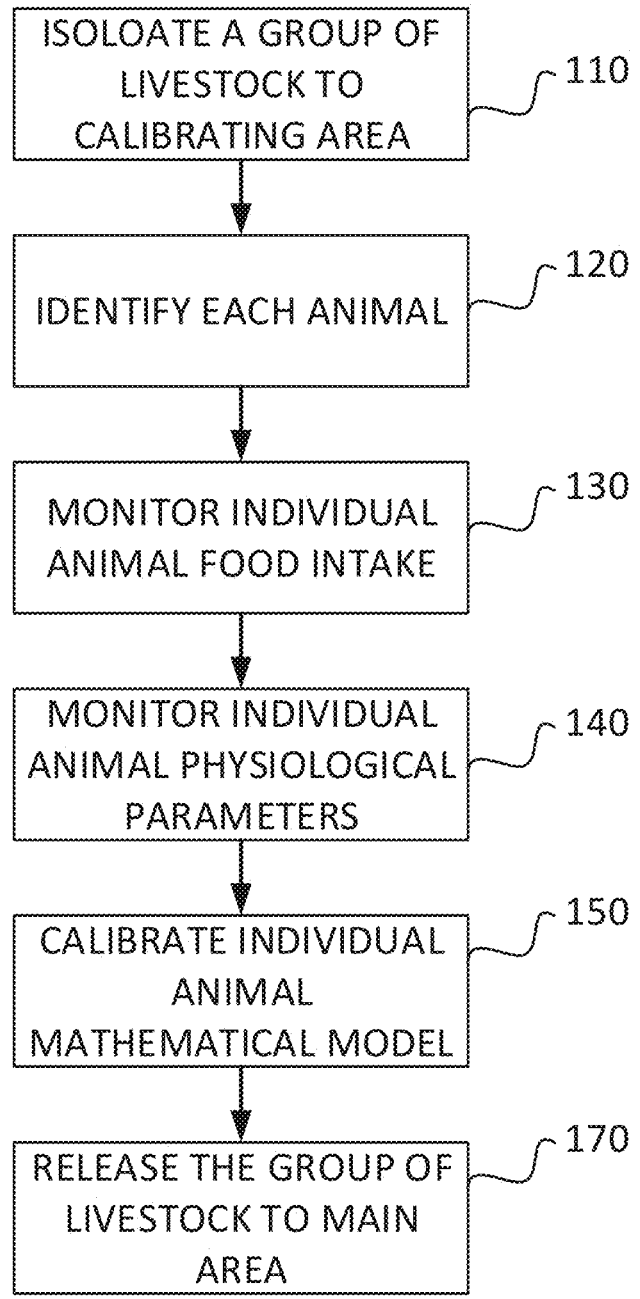
FIG. 3 is a simplified flow chart of an example method to determine individual animal mathematical model in accordance with some example embodiments.

FIG. 3 is a simplified flow chart of an example method to determine individual animal mathematical model in accordance with some example embodiments. According to some example embodiments, a group of animals from the herd or transferred to a designated area (section 250 shown in FIG. 1) for monitoring feed-intake and calibrating the mathematical model (equation 1) (block 110). Each animal is identified as it approaches a feeding station (block 120). According to some example embodiments, individual food intake is measured (block 130) while the animal eats at an individual feeding station. Time of meal and duration of meal is also monitored, e.g. with the identification system 270 or other tracking system. According to some example embodiments, each feeding station includes a dedicated scale and weight of fodder in the feeding station before and after an animal eats is compared to determine weight of food intake. According to some example embodiments, additional physiological parameters are determined or accessed from a remote site (block 140). In some example embodiments, physiological parameters may include the parameters in Equation (1) such as milk yield, fat percentage in milk, days in milking after calving, protein percentage in milk, number of lactations, animal weight, NRC ratio between body weight and milk yield and activity. According to some example embodiments, the mathematical model is calibrated based on data from the calibration period and the physiological data (block 150). During calibration, the coefficients in the mathematical model are defined for an individual animal. At the end of the calibration period, the animals are transferred to the general shed area and a new group of animals are transferred to the isolated area for calibrating (block 170).

Figure 4:
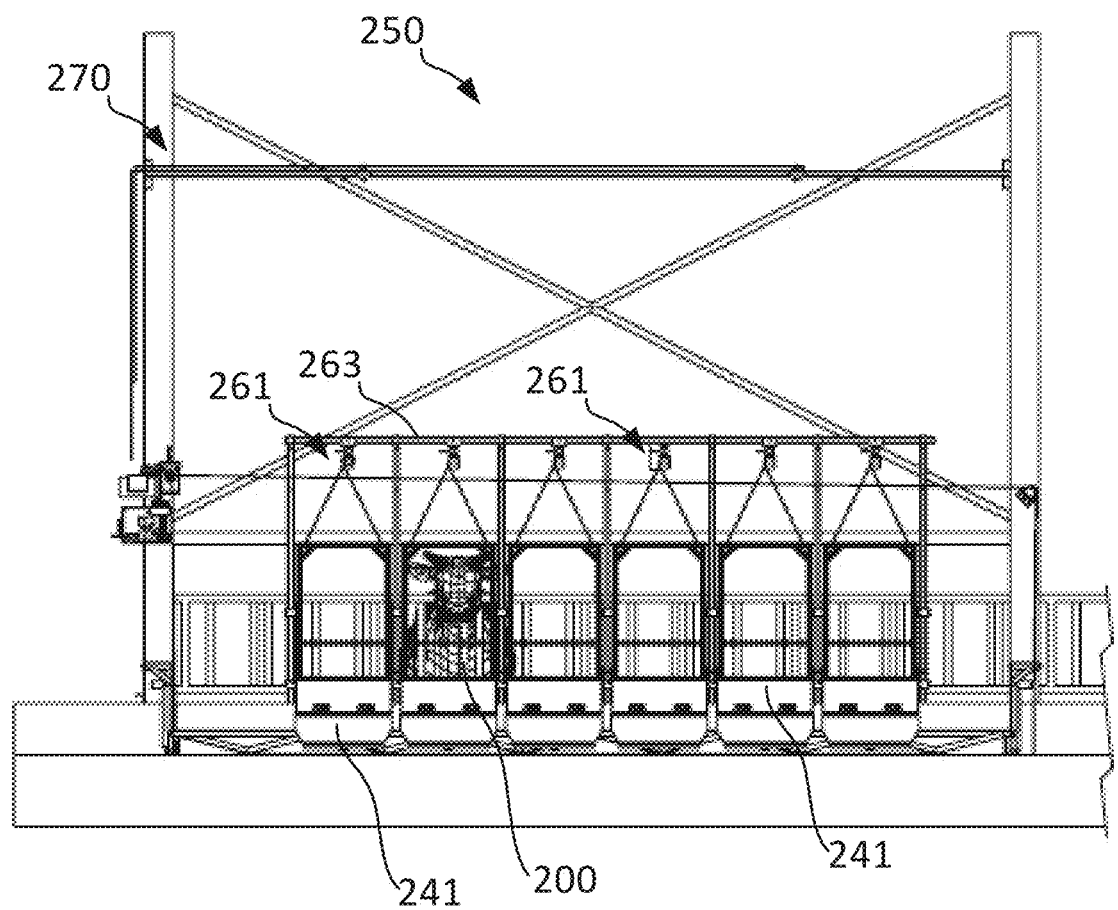
FIG. 4 is an example drawing of example feeding stations in a designated area in a livestock shelter for measuring food intake in accordance with some example embodiments.

FIG. 4 is an example drawing of example feeding stations in a designated area in a livestock shed for monitoring food intake in accordance with some example embodiments. According to some example embodiments, an isolated area 250 of a shed 210 includes a plurality of individual feeding stations 241, each feeding station including a feeding bin that is suspended from a frame 263 with a load cell 261. By suspending feeding bins, one load cell 261 per feeding station may be sufficient to monitor weight in the feeding bin. This may reduce the cost as compared to feeding stations that are supported on the ground and generally require at least two load cells for monitoring weight. According to some example embodiments, area 250 additionally includes an identification system 270. Optionally, identification system 270 is positioned above frame 263, optionally at a height of about 2.5-3.5 m, e.g. 3 m from the ground. Identification system 270 may identify and track eating behavior of more than one animal at a time. Optionally, identification system 270 includes a plurality of units, e.g. one unit per feeding station.

An example scale uses a 100 kg load cell with 50 g precision (L6G, Zemic Europe B.V., Etten-Leur, The Netherlands). The signal from the load cell may be amplified by a load cell amplifier (HX711, SparkFun Electronics, Boulder, Colorado) and read by a microcontroller (Uno, Arduino). Between 3-6 load cells may be connected to a computing system by the serial protocol.

Figure 5B:
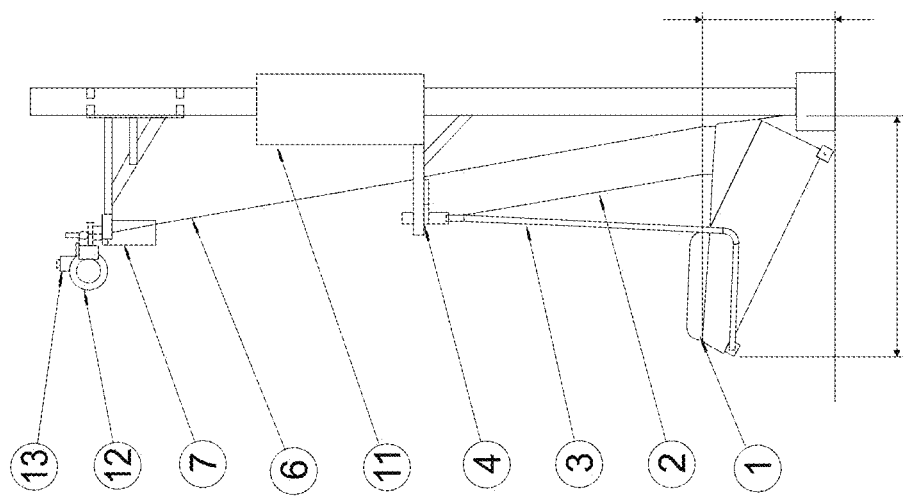
FIGS. 5A and 5B are front and side views of example suspended feeding stations in accordance with some example embodiments.
Figure 5A:
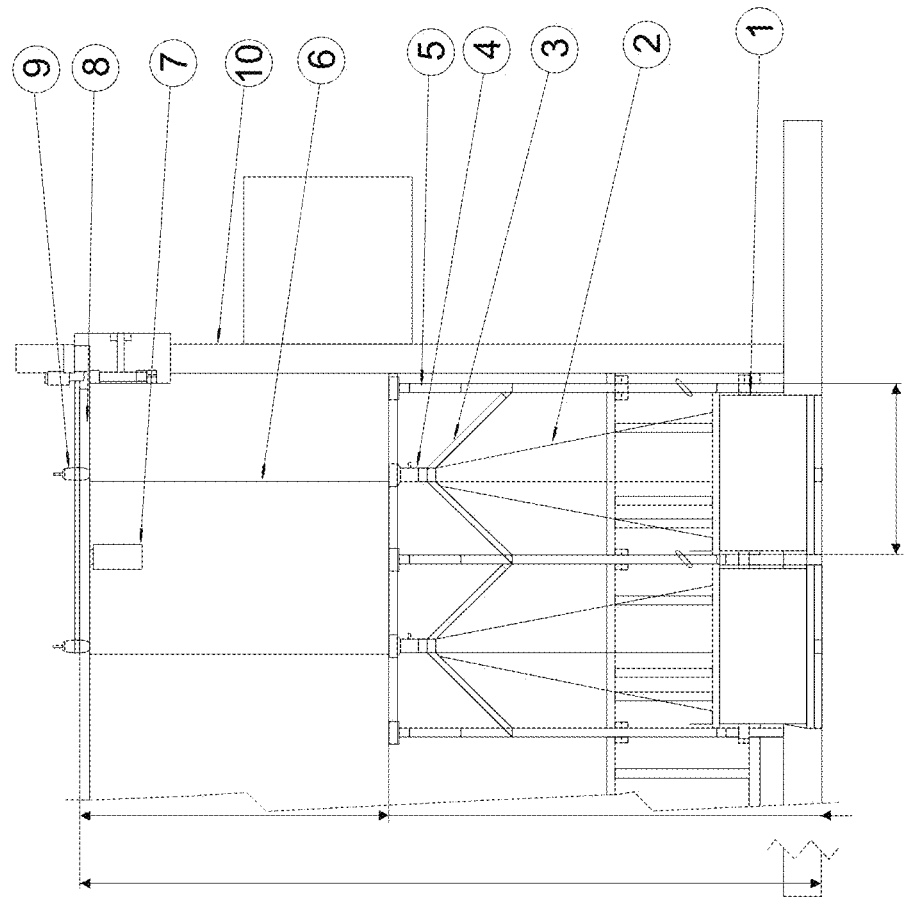

FIGS. 5A and 5B are front and side views of example suspended feeding stations in accordance with some example embodiments. Table 1 lists the various components that may optionally be included in feeding stations 241.

TABLE 1

List of components of the feeding station.

| Part No. | Description |
| --- | --- |
| 1 | Feeding bin |
| 2 | Rear cable |
| 3 | Frontal cable |
| 4 | Load cell |
| 5 | Scale frame |
| 6 | Lifting cable |
| 7 | Camera |
| 8 | Horizontal frame |
| 9 | Pulley |
| 10 | Cowshed column |
| 11 | Computer box |
| 12 | Lifting gear |
| 13 | Lifting motor |

According to some example embodiments, the camera together with the computer box is used to identify the animal. In some example embodiments, lifting motor 13 provides for tilting feeding bin 1 when it is desired to empty its contents.

Figure 6A:
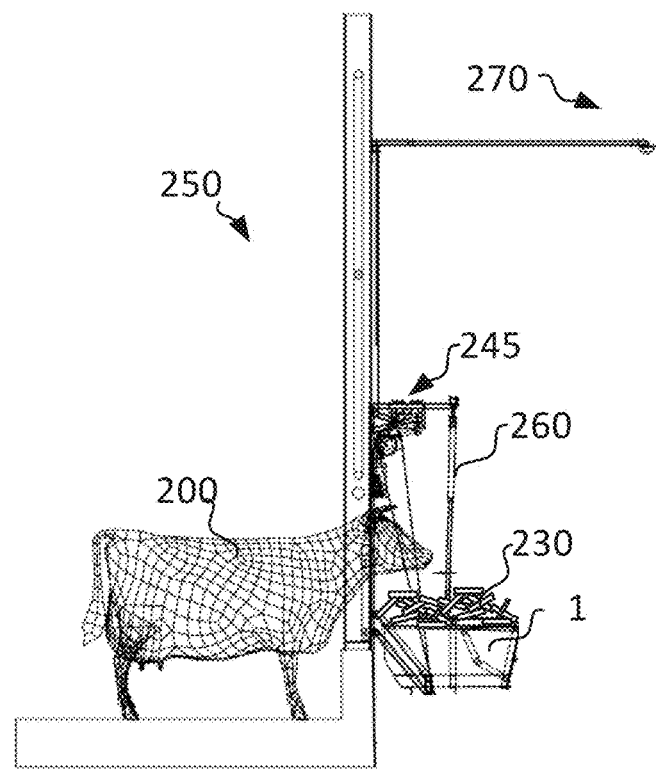
FIGS. 6A and 6B are side views of an example suspended feeding station in a feeding position and in a emptying position respectively in accordance with some example embodiments.
Figure 6B:
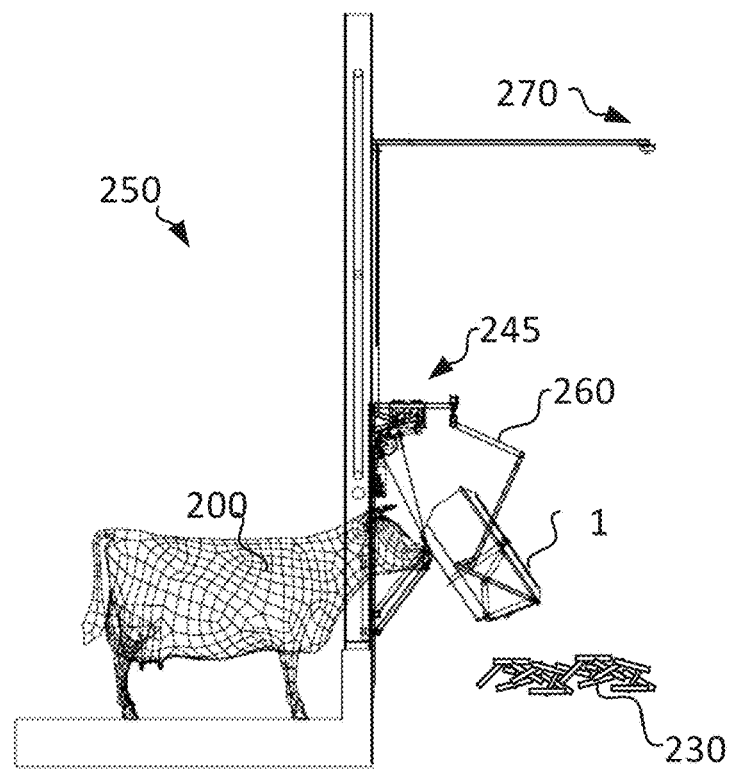

FIGS. 6A and 6B are side views of an example suspended feeding station in a feeding position and in an emptying position respectively in accordance with some example embodiments. In FIGS. 6A and 6B, the mechanical features 245 configured for tilting feeding bin 1 is shown. By suspending feeding bin 1 and providing for lifting and tilting with the motor and lifting gear, a tractor may be able to access the ground below and around feeding bin 1 to clean the area. This may makes cleaning more convenient and may save time that would otherwise be needed to manually clean around a feeding bin.

The remnants of the feed must be removed from the feeding area to prevent the putrefaction and appearing of insects and rodents. Similar to existing feed scales. In some example embodiments, a DC motor (Bosch CHP 24V 24W) with a 1:10 gear installed on frame 5 and connected to the feeding bins by cables through pulleys are used for turning over the bins by lifting their rear part. The motor and the gear are sufficient for lifting 6 bins with 5 kg of feed remnants. The lifting is performed until a terminal position defined by a micro switch installed on the cable. The view of the turned over scales in the terminal cleaning position is show in FIG. 6B.

During the eating, saliva of cows generates conglomerates of the feed, which remain stuck on the walls of the bin. Thus, turning over the feeding bin may be insufficient for clearing without labor assistance. The concentration of the conglomerates is located on the lower edge of the bin, where they fall and thereafter are pressed by the cow. In some example embodiments, feeding bin 1 has a turning clearing plate at the edge, where the conglomerates are collected. Optionally, the clearing plate turns on an axis during the bin turning over and removes the conglomerates.

Figure 7A:
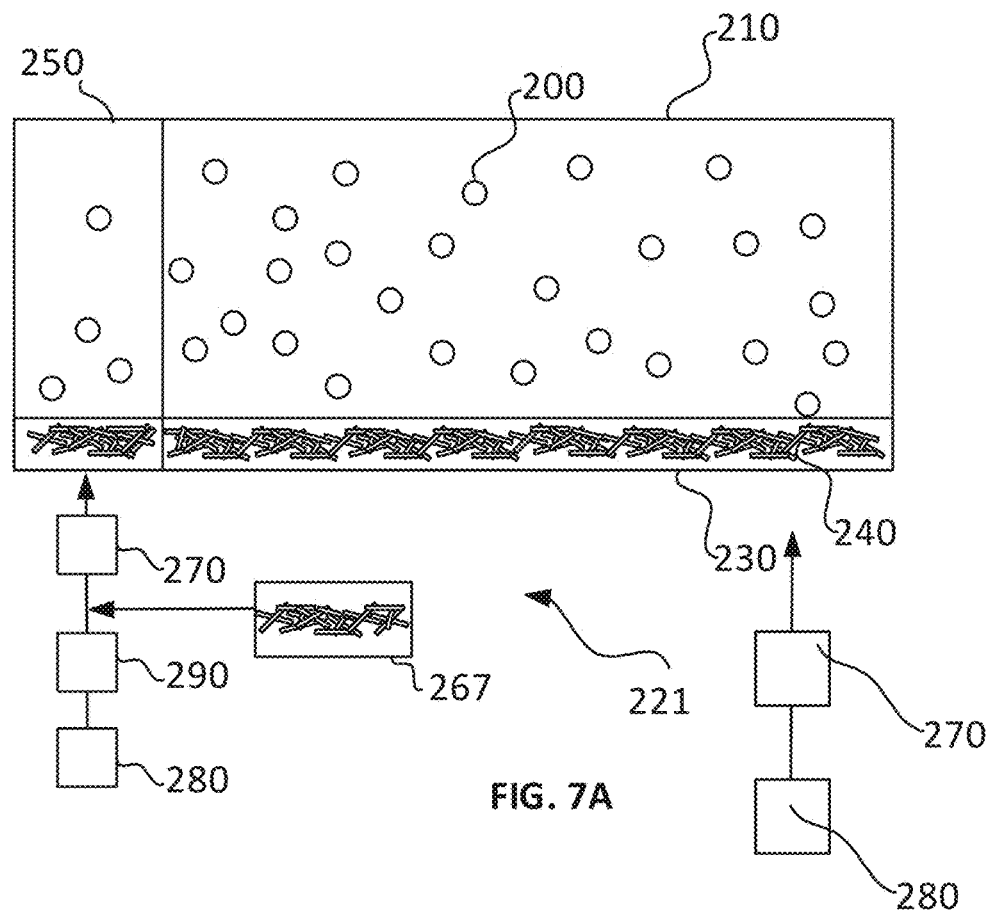
FIGS. 7A and 7B are two simplified block diagrams of other example livestock sheds including, both including a fodder volume sensing system in accordance with some example embodiments.
Figure 7B:
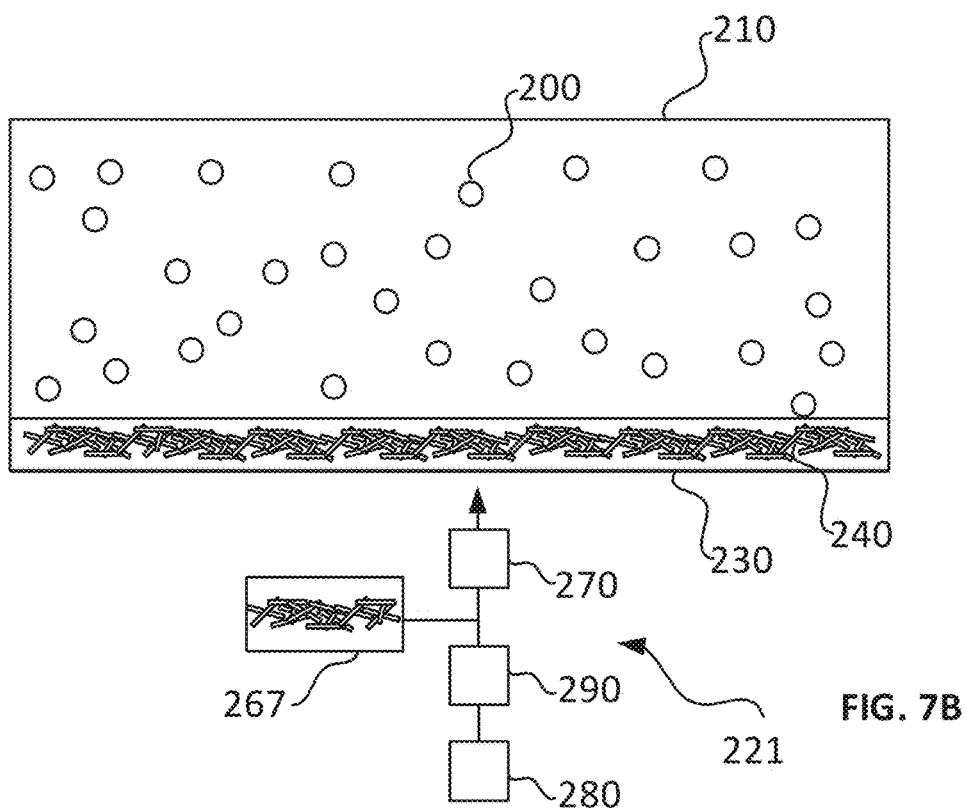

FIGS. 7A and 7B are two simplified block diagrams of other example livestock sheds including, both including a fodder volume sensing system in accordance with some example embodiments. According to some example embodiments, food intake may be monitored based on monitoring volume of the fodder as opposed to weight of the fodder. Measuring fodder intake based on volume eliminates the need for scales integrated with individual feeding stations. According to some example embodiments, food intake is monitored in a designated calibrating area 250 that occupies a small portion of shed 210, e.g. 10%-30% or 20% of shed 210 as shown in FIG. 7A. Volume detection may be performed with an imaging device 290, e.g. a depth camera or a plurality of cameras spread around a portion of feeding lane 230 in area 250.

In some example embodiments, a photogrammetric method is applied to detect volume of fodder. Photogrammetric method is an image processing algorithm. It is intended to create a 3D model of a surface of an object by a number of pictures of the object. The photogrammetric method may use pictures of the object achieved from different camera locations and may process the images to find features (tie points), which are common for a number of pictures, and performs the triangulation for the tie points to find their coordinate in the space.

In some example embodiments, volume detection may be performed with an off the shelf scanner such as PhotoModeler Scanner, developed by Eos Systems Inc. in Boston, Massachusetts.

In other example embodiments, when applying volume detection to determine food intake, a designated area 250 in which only a portion of the animals are monitored at any one time is not used and instead the entire feeding lane may be monitored as shown in FIG. 7B. The decision to monitor food intake as shown in FIG. 7A or FIG. 7B may for example depend on cost of the imaging system or scanner required for monitoring the volume. In some example embodiments, volume may be determined based on image processing of images of the fodder that have been captured as optionally images of reference points at defined heights.

In some example embodiments, when monitoring food intake based on volume, density or specific weight of the fodder is also monitored so that the weight of the food intake may be determined. Optionally, a dedicated scale 267 is included to detect weight of fodder. Density or specific weight may change over a course of a day due to partial dehydration of the fodder and may change day by day due to different types of fodder provided.

According to some example embodiments, the food intake calibration system 221 includes a weighing system 267 configured to monitor weight of fodder, identification system 270 configured to identify each cow approaching feeding lane 230, an imaging system 290 configured to monitor volume of fodder in front of the identified animal before and after the animal eats, and a computing system 280 configured to control the system operation, process data sampled and calibrate a mathematical model relating animal physiological parameters and eating behavior to food intake based on data sampled, e.g. the model defined in Equation 1. Identification system 270 may be based on RFID, may be based on biometric detection or may be based on identifying a visual tag on animal 200. According to some example embodiments, computing system 280 includes memory capability or access to remote memory. In some example embodiments computing system 280 is configured to store or access physiological data related to each animal 200 in section 250.

Referring now specifically to FIG. 7A, according to some example embodiments, each animal in a shed is monitored for efficiency or food intake for a relatively short portion of the lactation cycle. Optionally, calibrating occurs over a 2 week period or a period between 1-3 weeks. In some example embodiments, food intake representative of the entire lactation period may be determined based on output over the calibration period, tracking of animal eating behavior and physiological parameters over the rest of the lactation period and the mathematical model defined by Equation 1. Measurements taken while the animal is in designated area 250 may be used to calibrate the mathematical model for the animal and that mathematical model may be used to determine food intake of the animal for the entire lactation period in the main area of shed 210.

Figure 8:
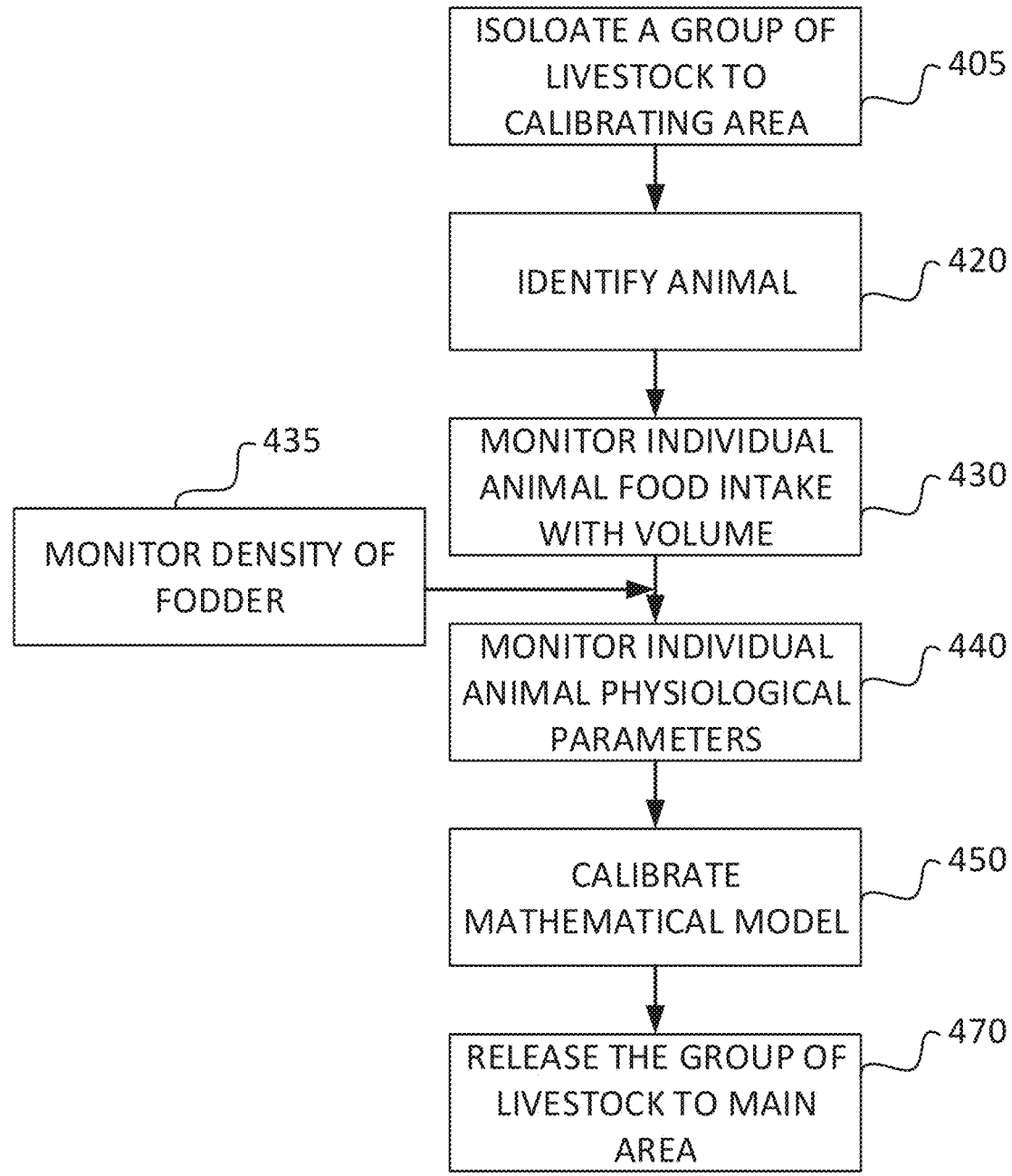
FIG. 8 is another simplified flow chart of another example method to determine individual animal mathematical model in accordance with some example embodiments.

FIG. 8 is another simplified flow chart of another example method to determine individual animal mathematical model in accordance with some example embodiments. According to some example embodiments, a group of animals from the herd or transferred to a designated area (section 250 shown in FIG. 7A) for monitoring food intake and calibrating the mathematical model (equation 1) (block 110). An animal approaching or at a feeding lane may be identified by an animal identification system (block 420). The animal identification system may be RFID device or an imaging device with processing. Image processing may be based on identifying biometrics or identifying an identification tag on the animal. Volume of fodder in the feed lane may be determined by imaging for example with a depth camera, three-dimensional camera or with a plurality of cameras capturing images from different angles (block 430). Optionally, a photogrammetry method may be applied. Optionally, reference objects are positioned around feeding lane to calibrate the images captured. According to some example embodiments, density or specific weight of the fodder is monitored by weighing a sample volume on a scale (block 435).

According to some example embodiments, additional physiological parameters are determined or accessed from a remote site (block 140). In some example embodiments, physiological parameters may include the parameters in Equation (1) such as milk yield, fat percentage in milk, days in milking after calving, protein percentage in milk, number of lactations, animal weight, NRC ratio between body weight and milk yield and activity. According to some example embodiments, the mathematical model is calibrated based on data from the calibrating period, collected data related to eating behavior and known or determined physiological data (block 450). During calibration, the coefficients in the mathematical model are defined for an individual animal. At the end of the calibrating period, the animals are transferred to the general shed area and a new group of animals are transferred to the isolated area for calibrating (block 470).

Figure 9:
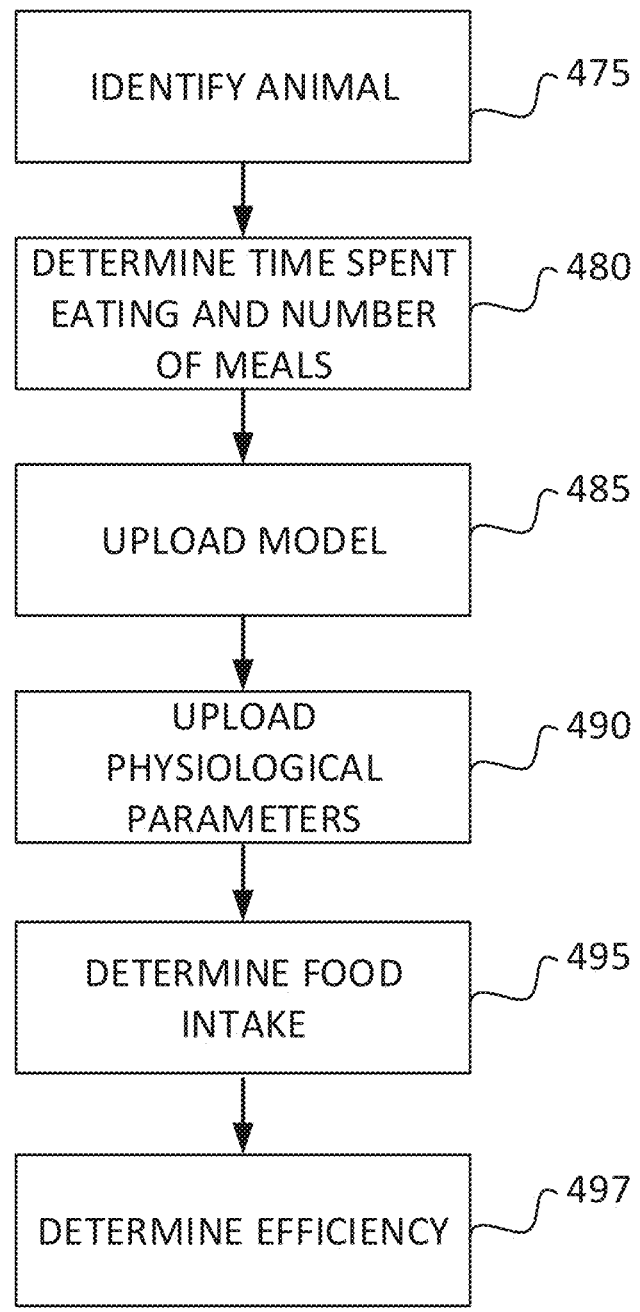
FIG. 9 is a simplified flow chart of an example method to monitor efficiency of an animal based on a mathematical model in accordance with some example embodiments.

FIG. 9 is a simplified flow chart of an example method to monitor efficiency of an animal based on a mathematical model in accordance with some example embodiments. According to some example embodiments, while an animal is in the main portion of the shed, the animal may be identified as it approaches a feeding lane (block 475). Eating parameters such as time spent eating and number of meals may be detected and stored (480). Detection of these eating parameters may typically be performed with relatively low cost equipment, e.g. cameras. Optionally at an end of a lactation period, the mathematical model for an animal may be uploaded (block 485). Physiological parameters of mathematical model for the animal may also be uploaded (block 490) and food intake may be determined (block 495). Efficiency may be defined based on the food intake and milk yield (block 497).

Figure 10:
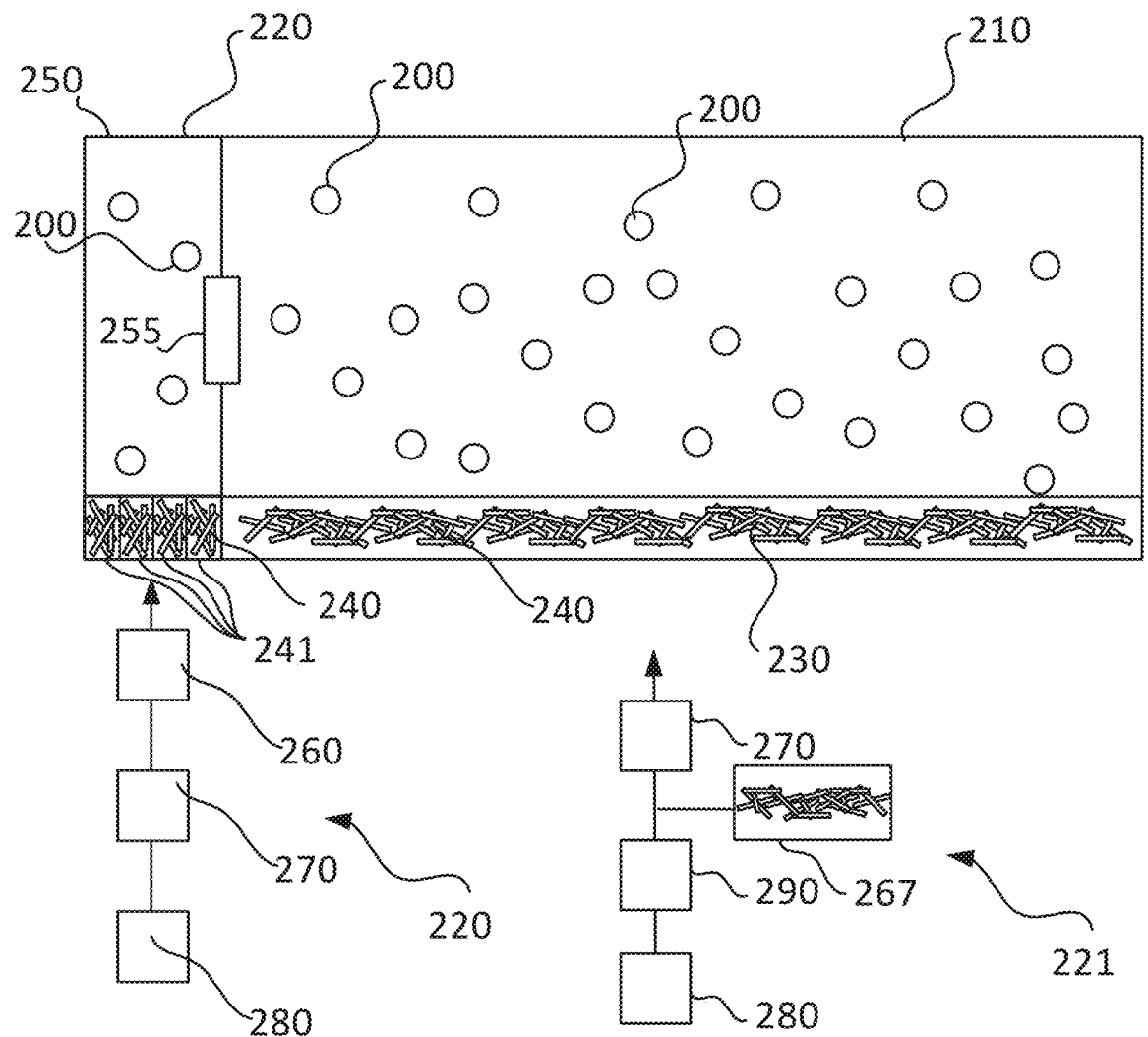
FIG. 10 is a simplified block diagram of an example livestock shelter including both a designated food intake calibrating area and a fodder volume sensing system in accordance with some example embodiments.

FIG. 10 is a simplified block diagram of an example livestock shelter including both a designated food intake calibrating area and a fodder volume sensing system in accordance with some example embodiments. In some example embodiments, a shed 210 may include a designated calibrating area 250 as described in reference to FIGS. 1 and 3 and may also include volume sensing system in a main area of shed 210 as described in reference to FIG. 7B. In some example embodiments, accuracy may be improved based on complementing information obtained from system 220 with the information obtained from system 221.

Figure 11:
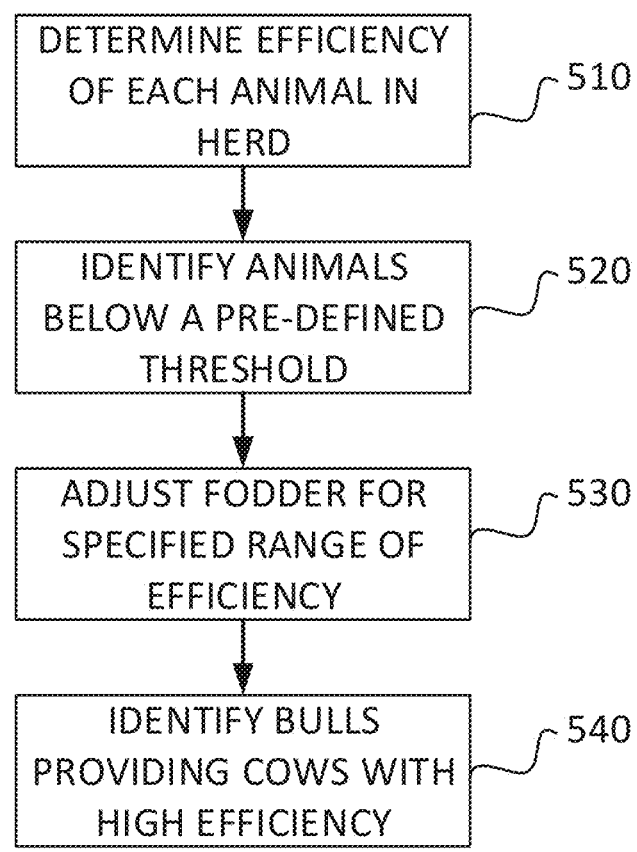
FIG. 11 is a simplified block diagram for herd management in accordance with some example embodiments.

FIG. 11 is a simplified block diagram for herd management in accordance with some example embodiments. In some example embodiments, a measure of animal efficiency is defined for each animal in a herd based on food intake in relation to milk output (block 510). In some example embodiments, animals that have efficiency below a pre-defined threshold are removed from the herd (block 520). In some example embodiments, fodder may be adjusted for specific groups of herds based on their efficiency measure (block 530). Optionally, animals with higher efficiency may be fed with more expensive or higher quality fodder. Alternatively, animals with lower efficiency may be fed with fodder to help improve their efficiency. In some example embodiments, a measure of efficiency may be applied to decide which bulls to use for future insemination (block 540).

What is claimed is:

1. A system for monitoring individual food intake of a livestock animal comprising:
 a calibration system installed in association with a first feeding station of a plurality of feeding stations of an animal shelter,
  wherein said plurality of feeding stations is divided between at least two separated areas of said animal shelter, wherein a first area of said at least two separated areas is a calibration area, in which said first feeding station of the plurality of feeding stations is located,
  wherein a second area of said at least two separated areas is a tracking area, in which a second feeding station of the plurality of feeding stations is located,
  wherein said calibration system is configured to measure weight of food intake or volume of food of food intake, of each of at least one animal over a pre-defined period of time and wherein said calibration system is configured to calibrate a mathematical model, specific for each of the at least one animal, based on the measure,
  wherein the mathematical model relates eating behavior of each of the at least one animal and defined physiological parameters of the respective animal with a respective food intake, and
  wherein the pre-defined period of time is less than three weeks;
 a tracking system installed in association with said second feeding station of the plurality of feeding stations in the animal shelter and is configured to track animal eating behavior at times other than the pre-defined period of time, while said tracked animal is in said second feeding station of the plurality of feeding stations; and a computing system configured to determine food intake of each of the at least one animal in the second feeding station of the plurality of feeding stations over a lactation period of the respective animal, based on the mathematical model for the respective animal as calibrated by the tracking system for the respective animal, and further based on the eating behavior at the times other than the pre-defined period of time, without measuring the weight of the food intake and without measuring the volume of the food intake.

2. The system of claim 1, wherein the calibration system is configured to service less than 20% of the livestock animals at a time.

3. The system of claim 1, wherein the calibration system is configured to be stationed in an isolated portion of the animal shed.

4. The system of claim 3, wherein the second feeding station of the plurality of feeding stations includes a common feeding lane in a portion of the animal shed that is not isolated.

5. The system of claim 1, wherein the first feeding station of the plurality of feeding stations includes a plurality of individual feeding stations, each integrated with a scale for measuring weight of food of food intake.

6. The system of claim 5, wherein at least one of the first feeding station of the plurality of feeding stations includes a feeding bin suspended from a frame with a first cable, and wherein the feeding station includes a load cell connected to the first cable.

7. The system of claim 6, wherein a second cable is connected at one end to the feeding bin and at another end to a lifting mechanism, wherein the lifting mechanism is configured to tilt the feeding bin and expel the food in the feeding bin based on pulling the second cable and wherein the feeding bin includes clearing plate that rotatable connected to the feeding bin, wherein the clearing plate is configured to rotate during tilting of the feeding bin.

8. The system of claim 1, wherein the calibration system comprises an imaging system configured to detect volume of fodder, wherein the imaging system includes at least one depth camera and is configured to apply a photogrammetric method to detect the volume and wherein the calibration system comprises a scale configured to monitor weight of a sample volume of fodder.

9. The system of claim 1, wherein the calibration system comprises an identification system configured to identify an animal eating and to monitor eating behavior of the animal, wherein the identification system is configured to identify the animal based on imaging a dedicated symbol on a collar of the animal, biometric verification or RFID.

10. The system of claim 1, wherein the calibration system comprises a computing system configured to calibrate the mathematical model and wherein the computing system is configured to access physiological data related to the animal.

11. The system of claim 1, wherein the mathematical model is animal specific.

12. A method for monitoring individual food intake of a livestock animal comprising:
measuring a weight of food of food intake of an animal in a herd while the animal is confined to eating at a first feeding station of a plurality of feeding stations in an animal shelter for a pre-defined period of time of less than three weeks,
wherein said plurality of feeding stations is divided between at least two separated areas of said animal shelter, wherein a first area of said at least two separated areas is a calibration area, in which said first feeding station of the plurality of feeding stations is located,
wherein a second area of said at least two separated areas is a tracking area, in which a second feeding station of the plurality of feeding stations is located;
tracking eating behavior of the animal during the pre-defined period of time;
calibrating a mathematical model, specific for the animal, based on the measuring, wherein the mathematical model relates the eating behavior of the animal and defined physiological parameters of the animal with the food intake;
tracking animal eating behavior at said second feeding station of the plurality of feeding stations in the animal shelter at times other than the pre-defined period of time; and
determining food intake of the animal at the second feeding station of the plurality of feeding stations, based on:
the mathematical model specific for the animal as calibrated for said animal,
the eating behavior at the second feeding station of the plurality of feeding stations and
without measuring the weight of the food intake.

13. The method of claim 12, comprising measuring the food intake of less than 20% of the livestock animals at a time.

14. The method of claim 12, comprising measuring food intake of other animals in the herd at the end of the pre-defined period of time and calibrating the mathematical model for each of the other animals over a subsequent pre-defined period.

15. The method of claim 12, wherein the measuring performed in an isolated portion of an animal shed.

16. The method of claim 12, wherein the measuring a weight of food of food intake of the animal is based on measuring weight of fodder in the first feeding station of the plurality of feeding stations and wherein the feeding station is integrated with an identification system configured to identify the animal eating.

17. The method of claim 12, wherein measuring food intake of the animal is based on detecting volume of fodder and monitoring specific weight of fodder, both in the first feeding station of the plurality of feeding stations, wherein the volume is detected based on a photogrammetric method.

18. The method of claim 12, wherein the mathematical model is animal specific.

19. The method of claim 12, wherein the defined physiological parameters of the animal includes days in milking, parameters defining milk quality of milk provided by the animal, and weight of the animal.

20. The method of claim 19 wherein the mathematical model relates amount of time the animal spends active with food intake and wherein the time the animal spends active is tracked.

21. The method of claim 12, wherein the eating behavior is tracked based on time spent eating and number of meals.

22. The method of claim 12, wherein the animals are cows.

* * * * *